United States Patent [19]

Watts

[11] 3,996,258
[45] Dec. 7, 1976

[54] ALCOHOL-ETHER SUBSTITUTED TETRAHALO BENZONITRILES

[75] Inventor: Lewis Watts, Austin, Tex.

[73] Assignee: Texaco Development Corporation, New York, N.Y.

[22] Filed: Sept. 2, 1975

[21] Appl. No.: 609,270

[52] U.S. Cl. .............................. 260/465 F; 71/103; 71/105; 71/122; 424/304; 424/337; 424/341; 260/607 A; 260/613 B

[51] Int. Cl.² ...................................... C07C 121/75

[58] Field of Search ..................... 260/465 F, 613 B

[56] References Cited

UNITED STATES PATENTS

| | | | |
|---|---|---|---|
| 2,416,263 | 2/1947 | Mac Mullen | 260/613 |
| 2,569,883 | 10/1951 | Doelling et al. | 260/613 X |
| 2,949,488 | 8/1960 | Rocklin | 260/613 X |
| 3,798,255 | 3/1974 | Watts, Jr. | 260/465 F |

Primary Examiner—Lewis Gotts
Assistant Examiner—Dolph H. Torrence
Attorney, Agent, or Firm—Carl G. Ries; Thomas H. Whaley; James L. Bailey

[57] ABSTRACT

Covers compounds of the formula

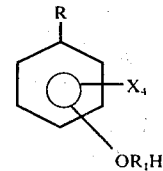

where R is selected from the group consisting of cyano, nitro and lower alkyl sulfone, X is halo, and $R_1$ is $-CH_2CH_2O-_y$ where $y$ is 1–3 or $R_2$ O where $R_2$ is a straight or branched chain alkylene radical containing 2–6 carbon atoms. Also covers a method of preparing said above compounds by reacting

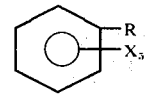

with $OHR_1H$, where R, X, and $R_1$ have a significance as above for sufficient time to produce the desired compound. These alcohol-ether substituted aromatics have biological activity and are also useful as chemical intermediates.

3 Claims, No Drawings

ALCOHOL-ETHER SUBSTITUTED TETRAHALO BENZONITRILES

BACKGROUND OF THE INVENTION

1. Field of the Invention

The invention relates to new chemical compositions of matter, their synthesis and their biological uses.

2. Description of the Prior Art

In U.S. Pat. No. 3,056,843 there is disclosed the formation of di and triols via the treatment of hexahalobenzenes in the presence of base with polyols containing 3 or 4 hydroxy groups respectively.

British Pat. No. 835,499, entitled "Process for Producing Halogen-Containing Aromatic-Aliphatic Polyethers", is concerned with a process for the production of halogencontaining aromatic-aliphatic polyethers wherein polyhalogen aromatics are reacted with aliphatic, cyclo-aliphatic or aromatic-aliphatic diols with a molecular weight of at least 104 in the presence of alkali.

U.S. Pat. No. 2,692,899 describes the use of alkanediols in general and ethylene glycol in particular for the conversion of hexachlorobenzene to pentachlorophenol.

While the above references are generally concerned with the type of compounds made here, such prior art does not disclose how to simply and economically achieve etheralcohol substituted tetrahalo aromatic compounds containing in addition an activating group such as cyano and the like. Heretofore, reactions of the type encompassed here led to polysubstitution of the aromatic ring with the glycol reactant to form polyhydroxyether compounds by replacement of more than one halo atom, and/or further reaction of the aromatic reactant with the glycol ether aromatic through further halo replacement to produce a coupled diaromatic compound. And in some instances such reaction of the polyhalo aromatic compound led to formation of polyhalophenols rather than the hydroxy ether derivative.

It will therefore be a substantial advance in the art if a new class of alcohol-ether substituted tetrahalo aromatic compounds could be made via a single, relatively economical scheme which did not produce byproducts of the type just discussed through other theoretically possible reaction schemes.

SUMMARY OF THE INVENTION

New compounds of the formula

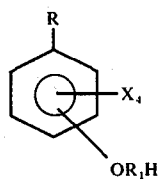

where R is selected from the group consisting of cyano, nitro and lower alkyl sulfone, X is halo, and $R_1$ is $+CH_2CH_2O+_y$ where $y$ is 1–3 or $R_2O$ where $R_2$ is a straight or branched chain alkylene radical containing 2–6 carbon atoms. These compounds are prepared by the reaction of a compound

with $OHR_1H$ where R, X and $R_1$ have a significance as just expressed. These compounds are particularly useful as biological chemicals such as to control undesirable vegetation as pre-emergence and post-emergence herbicides and as soil and foliar fungicides.

DESCRIPTION OF THE PREFERRED EMBODIMENT

The new alcohol-ethers of my invention are prepared by the interaction of a pentahalo aromatic compound also containing a strong activating group such as cyano with a glycol or glycol ether. Surprisingly, only one halo atom is replaced on the aromatic ring by reaction with the glycol to produce a monosubstituted hydroxyether compound. No polysubstition such as di or tri substitution was noted, as one would expect. Also, even though the resultant products were strongly nucleophilic they did not further react with another pentahalo aromatic compound such as pentachlorobenzonitrile to produce a coupled product or diether diaromatic compound. Thus, the reaction is surprisingly selective for preparation of only a monosubstituted alcohol ether with no mixture of mono and polysubsubstituted compounds being made. Such advantage in preparing a single isolatable compound rather than a mixture of polysubstituted aromatics and coupled products is an obvious advance in the art.

The aromatic reactant may be any pentahalo aromatic containing in addition a strong activating group such as cyano, nitro, lower alkyl sulfone, etc. When such group is a lower alkyl sulfone such lower alkyl group contains 1–4 carbon atoms, and most preferably is methyl or ethyl. A preferred reactant is pentahalo benzonitrile, and particularly pentachlorobenzonitrile which may be prepared according to the procedure of U.S. Pat. No. 3,855,264. While the chlorosubstituted compounds are preferred reactants, the reaction here may also be run with pentabromo, and pentafluoro aromatics.

The glycol or glycol ether compounds may be chosen from a considerable number of compounds of this type including ethylene glycol, propylene glycol, petamethylene glycol, hexamethylene glycol, diethylene glycol, triethylene glycol, etc.

The reaction itself is usually run in the presence of a strong base such as an alkali or alkaline earth metal hydroxide or an alkali or alkaline earth metal hydride. Tertiary amines, including aromatic tertiary amines may also function as catalysts in the reaction described herein. Preferred are sodium or potassium hydride.

Depending upon the type of reactants and other variables the time and the temperature of reactions may be widely varied. Usually the reaction is complete within a time ranging from ¼ to about 10 hours when carried out at 0°–100° C. More often, the reaction is run at 10°–35° C. for ½–5 hours.

The following example illustrates preparation of a typical compound of this invention. It is understood that this example is merely illustrative and that the invention is not to be limited thereto. While the proportions of the reactants may be somewhat varied, normally they are reacted on a molar basis in order to achieve the desired monohydroxy substituted aromatic compound.

EXAMPLE I

To solution of 34.4 grams of pentachlorobenzonitrile in tetrahydrofuran was added a mixture of 8.0 grams ethylene glycol, 8.0 grams of a 50% sodium hydride-mineral oil dispersion and 250 ml tetrahydrofuran. The resulting reaction mixture was heated at reflux for one hour and then poured into a large volume of water. Filtration afforded an almost colorless solid which was dissolved in tetrahydrofuran. Treatment with magnesium sulfate followed by filtration and removal of the solvent gave rise to beta-hydroxyethoxy-tetrachlorobenzonitrile. This material is identical basis both nmr and infrared spectral data to the product formed from the reaction of tetrachlorocyanophenol with ethylene oxide as set forth below.

Specifically, to a one liter stainless steel pressure vessel was charged 130 grams of pentachlorobenzonitrile, 200 ml of toluene, and 2 ml of concentrated ammonium hydroxide. While the resulting mixture was maintained at about 110° C., 28.6 grams of ethylene oxide was added over a period of three hours. From the resulting crude reaction mixture there was isolated a solid material which upon crystallization exhibited the following elemental analysis: Calculated for $C_9H_5Cl_4NO_2$; 35.91%C, 1.67%H, 47.11%Cl, 4.65%N. Found; 35.77%C, 1.66%H, 5.61%N, 46.61%Cl.

The compounds of my invention are useful biological chemicals, particularly by controlling undesirable vegetation by way of acting as pre-emergent or postemergent herbicides. The compounds are also useful foliar or soil fungicides.

In one series of tests, soil fungicidal activity of the compounds of the invention was evaluated by means of discrete soil-borne fungi. The test organisms were raised in sterile soil cultures to which have been added 20% by weight of cornmeal. The soil to be used for dilution purposes was separately sterilized by means of methyl bromide. The pure culture soil to be used for test purposes was then prepared by admixing 10% by weight of the test organism inoculum with 90% by weight of sterilized soil. The test soil was then aliquoted in 50 gram quantities to 3 replicated paper cups. Such soil was then treated with the chemical by drenching each cup with 10 milliliters of chemical. The chemical concentration is so adjusted that the 10-ml. quantity gave a dosage of 100 p.p.m. based on the weight of the soil (BW/S). The cups were held in a constant temperature-humidity cabinet for the duration of the test. In the absence of control masses of white mycelium (MCY) developed on the surface of the test vessels and control was readily evident visually. It is easy to recognize degrees of control based upon the extent of mycelial growth, and a rating scale of 10 to 0 is used, in which 10 indicates no mycelial growth to the other extreme where 0 indicates that no control is present.

Results of the soil fungicidal evaluation of the compound of Example I above is shown in Table I below.

TABLE I

| CHEMICAL | PYTHIUM-PEAS | | | RHIZOOCTONIA-BEETS | |
|---|---|---|---|---|---|
| | p.p.m. BW/S Dose | MYC Growth | Percent Stand | MYC Growth | Percent Stand |
| Example I | 100 | 6 | 70 | 0 | 50 |
| — | — | 0 | 0 | 0 | 10 |

I claim:
1. A compound of the formula

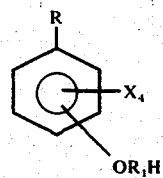

where R is cyano, X is halo, and $R_1$ is $-(CH_2CH_2O)_y-$ where y is 1–3 or $R_2O$ where $R_2$ is a straight or branched chain alkylene radical containing 2–6 carbon atoms.

2. The compound of claim 1 where X is chloro.
3. The compound of claim 1 where $R_1$ is $R_2O$ where $R_2$ is $—CH_2CH_2—$.

* * * * *